(12) United States Patent
Chen

(10) Patent No.: US 7,159,259 B2
(45) Date of Patent: Jan. 9, 2007

(54) GELATINOUS ELASTOMER COMPOSITIONS AND ARTICLES

(75) Inventor: John Y. Chen, Pacifica, CA (US)

(73) Assignee: Applied Elastomerics, Inc., South San Francisco, CA (US)

( * ) Notice: Subject to any disclaimer, the term of this patent is extended or adjusted under 35 U.S.C. 154(b) by 262 days.

(21) Appl. No.: 10/334,542

(22) Filed: Dec. 31, 2002

(65) Prior Publication Data

US 2003/0134958 A1    Jul. 17, 2003

Related U.S. Application Data

(63) Continuation-in-part of application No. 08/612,586, filed on Mar. 8, 1996, now Pat. No. 6,552,109, which is a continuation-in-part of application No. PCT/US94/04278, filed on Apr. 1, 1994, which is a continuation-in-part of application No. 08/211,781, filed on May 14, 1996, now Pat. No. 6,033,283, which is a continuation-in-part of application No. PCT/US94/07314, filed on Jun. 27, 1994, which is a continuation-in-part of application No. 08/256,235, filed on Jun. 27, 1994, now Pat. No. 5,868,597, and a continuation-in-part of application No. 08/288,690, filed on Aug. 11, 1994, now Pat. No. 5,633,286, and a continuation-in-part of application No. 08/581,188, filed on Dec. 29, 1995, now abandoned, and a continuation-in-part of application No. 08/581,191, filed on Dec. 29, 1995, now Pat. No. 5,760,117, and a continuation-in-part of application No. 08/581,125, filed on Dec. 29, 1995, now Pat. No. 5,962,572, said application No. 10/334,542 is a continuation-in-part of application No. 10/993,361, filed on Jul. 20, 2002, and a continuation-in-part of application No. 10/199,362, filed on Jul. 20, 2002, and a continuation-in-part of application No. 10/199,363, filed on Jul. 20, 2002, and a continuation-in-part of application No. 10/199,364, filed on Jul. 20, 2002, now Pat. No. 6,794,440, and a continuation-in-part of application No. 09/896,047, filed on Jun. 30, 2001, and a continuation-in-part of application No. 10/273,828, filed on Oct. 17, 2002, and a continuation-in-part of application No. 09/517,230, filed on Mar. 2, 2000, and a continuation-in-part of application No. 09/721,213, filed on Nov. 21, 2000, now Pat. No. 6,867,253, and a continuation-in-part of application No. 09/412,886, filed on Oct. 5, 1999, and a continuation-in-part of application No. 08/130,545, filed on Aug. 8, 1998, now Pat. No. 6,627,275, said application No. 09/412,886 is a continuation-in-part of application No. 08/984,459, filed on Dec. 3, 1997, now Pat. No. 6,324,703, and a continuation-in-part of application No. 08/130,545, filed on Aug. 8, 1997, now Pat. No. 6,627,275, and a continuation-in-part of application No. 08/909,487, filed on Aug. 12, 1997, now Pat. No. 6,050,871, and a continuation-in-part of application No. 08/863,794, filed on May 27, 1997, now Pat. No. 6,117,176, and a continuation-in-part of application No. 09/285,809, filed on Apr. 1, 1999, now abandoned, and a continuation-in-part of application No. 08/719,817, filed on Sep. 30, 1996, now Pat. No. 6,148,830, and a continuation-in-part of application No. 09/230,940, filed as application No. PCT/US97/17534 on Sep. 30, 1997, now Pat. No. 6,161,555, and a continuation-in-part of application No. 08/211,781, filed as application No. PCT/US94/04278 on Apr. 19, 1994, now Pat. No. 6,033,283, and a continuation-in-part of application No. 08/612,586, filed on Mar. 8, 1996, now Pat. No. 6,552,109, and a continuation-in-part of application No. 09/274,498, filed on Mar. 28, 1999, now Pat. No. 6,420,475, which is a continuation-in-part of application No. 08/954,424, filed on Oct. 20, 1997, now Pat. No. 6,333,374, which is a continuation-in-part of application No. 08/665,343, filed on Jun. 17, 1996.

(51) Int. Cl.
| | |
|---|---|
| C08K 5/01 | (2006.01) |
| B60R 21/26 | (2006.01) |
| B29C 67/20 | (2006.01) |
| B68G 11/04 | (2006.01) |
| C08F 1/28 | (2006.01) |

(52) U.S. Cl. .............................. 5/655.5; 5/653; 5/654; 5/909; 36/37; 36/43; 36/153; 264/46.4; 264/109; 264/113; 264/122; 264/211.13; 280/742; 310/309; 524/571

(58) Field of Classification Search ................ 310/309; 264/211.13, 113, 122, 109, 46.4; 524/571; 5/653, 654, 655.5, 909; 280/742; 428/304.4; 36/37, 43, 153

See application file for complete search history.

(56) References Cited

U.S. PATENT DOCUMENTS 6,027,674 A * 2/2000 Yates .......................... 264/113
6,413,458 B1 * 7/2002 Pearce ......................... 264/141

* cited by examiner

Primary Examiner—Herbert J. Lilling

(57) ABSTRACT

Novel gelatinous compositions and articles are formed from an intimate melt blend admixture of one or more of a selected block SEEPS copolymers in combination with one or more polymers of poly(styrene-butadiene-styrene), poly(styrene-butadiene)$_n$, poly(styrene-isoprene-styrene), poly(styrene-isoprene)$_n$, poly(styrene-ethylene-propylene), poly(styrene-ethylene-propylene-styrene)$_n$, poly(styrene-ethylene-butylene-styrene)$_n$, poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, and polyethylene, and a plasticizing oil.

20 Claims, No Drawings

GELATINOUS ELASTOMER COMPOSITIONS AND ARTICLES

ORIGINS OF INVENTION AND RELATED APPLICATIONS

This application is a continuation-in-part (CIP) of application Ser. No. 03/612,586 filed Mar. 8, 1996 (now U.S. Pat. No. 6,552,109) which is a continuation-in-part (CIP) of application: PCT/US94/04278 filed Apr. 19, 1994 (published May 26, 1995 No. WO95/13851, U.S. Ser. No. 08/211,781, now U.S. Pat. No. 6,033,283), and a CIP of PCT/US94/07314 filed Jun. 27, 1994 (published Jan. 4, 1996 No. WO 96/00118, U.S. Ser. No. 08/256,235, now U.S. Pat. No. 5,868,597), and a CIP of 08/288,690 filed Aug. 11, 1994 (now U.S. Pat. No. 5,633,286), and a CIP of 08/581,188 filed Dec. 29, 1995 (now abn.), and a CIP of 08/581,191 filed Dec. 29, 1995 (now U.S. Pat. No. 5,760,117), and a CIP of 08/581,125 filed Dec. 29, 1995 (now U.S. Pat. No. 5,962,572). This application is also a CIP of 10/199,361 filed Jul. 20, 2002, and a CIP of 10/199,362 filed Jul. 20, 2002, and a CIP of 10/199,363 filed Jul. 20, 2002, and a CIP of 10/199,364 filed Jul. 20, 2002 (now U.S. Pat. No. 6,794,440), and a CIP of 09/896,047 filed Jun. 30, 2001, and a CIP of 10/273,828 filed Oct. 17, 2002, and a CIP of 09/517,230 filed Mar. 2000, and a CIP of 09/721,213 filed Nov. 21, 2000 (now U.S. Pat. No. 6,867,253) and a CIP of 09/412,886 filed Oct. 5, 1999 (abn.), and a CIP of 08/130,545 filed Aug. 8, 1998 (now U.S. Pat. No. 6,627,275). In turn 09/412,886 filed Oct. 5, 1999 is a CIP of 08/984,459 filed Dec. 3, 1997 (now U.S. Pat. No. 6,324,703B1), and a CIP of 08/130,545 filed Aug. 8, 1998 (now U.S. Pat. No. 6,627,275), and a CIP of 08/909,487 filed Aug. 12, 1997 (now U.S. Pat. No. 6,050,871), and a CIP of 08/863,794, filed May 27, 1997 (now U.S. Pat. No. 6,117,176), and a CIP of 09/285,809 filed Apr. 1, 1999 (abn.), and a CIP of 08/719,817 filed Sep. 30, 1996 (now U.S. Pat. No. 6,148,830), and a CIP of 09/230,940 filed Sep. 30, 1997 PCT/US97/17534 (now U.S. Pat. No. 6,161,555), and a CIP of 08/211,781 filed Apr. 19, 1994 PCT/US94/04278 (now U.S. Pat. No. 6,033,283), and a CIP of 08/612,586 filed Mar. 8, 1996 (now U.S. Pat. No. 6,552,109), and a CIP of 09/274,498 filed Mar. 28, 1999 (now U.S. Pat. No. 6,420,475B1). In turn 09/274,498 filed Mar. 28, 1999 (now U.S. Pat. No. 6,420,475B1) is a CIP of 08/984,459 filed Dec. 3, 1997 (now U.S. Pat. 6,324,703B1), which is a CIP of 08/954,424 filed Oct. 20, 1997 (now U.S. 633374B1), which is a CIP 08/665,343 filed Jun. 17, 1996. The subject matter contained in the related applications and patents are incorporated herein by reference.

FIELD OF THE INVENTION

The present invention relates to useful gelatinous elastomer compositions and articles.

BACKGROUND OF THE INVENTION

This application is based upon subject matters described in earlier filed and copending related applications and patents (see Related Applications above) which are specifically incorporated herein by reference.

As taught in related U.S. Pat. No. 4,369,284, No. 4,618,213 and No. 5,153,254, oil extended thermoplastic block copolymers of the prior art suffer certain poor properties. Shell Technical Bulletin No. SC65-75 teaches the use of low viscosity poly(styrene-ethylene-butylene-styrene) triblock copolymers (Kraton G 1650 and G 1652) with Brookfield Viscosities of 1,500 and 550 cps (viscosity being measured for a solution of 20 weight percent solids in toluene at 25° C.) plasticized with oil, the compositions obtained trend to rupture and crumble when submitted to moderate shearing stress conditions.

SUMMARY OF THE INVENTION

The advantages and inherent properties of the gelatinous elastomer compositions (herein interchangeably refer to as "gelatinous compositions" or simply as "gel compositions" or more simply as "gels") and articles of the invention are many. The gel compositions and articles exhibits high dimensional stability, crack, tear, craze, and creep resistance, excellent tensile strength and high elongation, long service life under stress and capable of repeated handling, excellent processing ability for cast molding, non-toxic, nearly tasteless and odorless, extremely soft and strong, highly flexible, possessing elastic memory, substantially with little or no plasticizer bleedout. The gel can also be made transparent. The desirable combination of physical properties are unexpected.

In a first embodiment, the composites of the invention comprises a thermoplastic, heat formable and heat reversible gelatinous elastomer composition, G, which is formed into a composite by heat and interlocked with one or more of a selected substrate material, M, said gelatinous elastomer composition formed from (I) 100 parts by weight of one or a mixture of two or more of a hydrogenated styrene isoprene/butadiene block copolymer(s) in combination with or without (II) a selected amount of one or more polymers or copolymers of poly(styrene-butadiene-styrene), poly(styrene-butadiene)$_n$, poly(styrene-isoprene-styrene)$_n$, poly(styrene-isoprene)$_n$, poly(styrene-ethylene-propylene), poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one;

(III) about 300 to about 1,600 parts by weight of a plasticizing oil; said gelatinous elastomer compositions characterized by a gel rigidity of from about 20 to about 800 gram Bloom; wherein said block copolymers have the general configuration A-B-A wherein A is a glassy polymer end block segment of polystyrene and B is an elastomeric polymer center block segment of (ethylene-ethylene-propylene) and wherein said composite formed from the combination $G_nM_n$, $G_nM_nG_n$, $M_nG_nM_n$, $M_nM_nG_n$, $G_nG_nG_nM_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_n$-$M_nG_n$, $G_nG_nM_nM_nG_n$, $G_nG_nM_nG_nM_nG_n$, a sequential addition or a permutation of one or more of said $G_n$ with $M_n$; wherein when n is a subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or a different gel rigidity of from about 20 to about 800 gram Bloom.

More generally, the invention comprises thermoplastic, heat formable and heat reversible gelatinous elastomer compositions and articles formed from (I) 100 parts by weight of one or more hydrogenated styrene block copolymers having 2-methyl-1,3-butadiene and 1,3-butadiene blocks of the formula poly(styrene-ethylene-ethylene-propylene-styrene) and optionally in combination with (II) a selected amount of one or more selected polymer or copolymer; (III) from about 300 to about 1,600 parts by weight of a plasticizing oil; said gelatinous elastomer compositions and articles being characterized by a gel rigidity of from about 20 to about 800 gram Bloom.

Useful articles can be formed from the gelatinous elastomer compositions of the invention, including molded articles, composites (gel compositions "interlocked" with various substrates), articles having sticking and non-sticking properties, strong oriented gel compositions as view in polarized light etc.

The various aspects and advantages of the invention will become apparent to those skilled in the art upon consideration of the accompanying disclosure.

DESCRIPTION OF THE PREFERRED EMBODIMENTS

A internet search of the USPRO Patent Data Base of Applicant's published patent applications and issued patent describing gel compositions useful for fishing identified: U.S. Pat. Nos. 6,161,555, 6,333,374; 6,324,703; 6,148,830; 6,117,176; 6,050,871; 5,884,639; 5,508,334; 5,334,646; 5,262,468; 5,153,254; PCT/US97/17534, PCT/US94/04278 and PCT/US94/07314 which are incorporated herein by reference.

As taught in my co-pending applications: 0/273828 and 0/1999364, and specifically incorporated herein, block and other copolymers are described in the following publications:

(1) W. P. Gergen, "Uniqueness of Hydrogenated Block Copolymers for Elastomeric Applications," presented at the German Rubber Meeting, Wiesbaden, 1983; Kautsch, Gummi, Kunstst. 37, 284 (1984). (2) W. P. Gergen, et al., "Hydrogenated Block Copolymers," Paper No. 57, presented at a meeting of the Rubber Division ACS, Los Angeles, Apr. 25, 1985. Encyclopedia of Polymer Science and Engineering, Vol. 2, pp 324–434, "Block Copolymers". (3) L. Zotteri and et al., "Effect of hydrogenation on the elastic properties of poly(styrene-b-diene-b-styrene) copolymers", Polymer, 1978, Vol. 19, April. (4) J. Kenneth Craver, et al., Applied Polymer Science, Ch. 29, "Chemistry and Technology of Block Polymers", pp. 394–429, 1975. (5) Y. Mahajer and et al., "The influence of Molecular Geometry on the Mechanical Properties of homopolymers and Block Polymers of Hydrogenated Butadiene and Isoprene" reported under U.S. ARO Grant No. DAAG29-78-G-0201. (6) J. E. McGrath, et al., "Linear and Star Branched Butadiene-Isoprene Block Copolymers and Their Hydrogenated Derivatives", Chem. Dept, Virginia Polytechnic Institute and State University Blacksturg, Va., reported work supported by Army Research Office. (7) Legge, Norman R., "Thermoplastic Elastomers", Charles Goodyear Medal address given at the 131st Meeting of the Rubber Division, American Chemical Society, Montreal, Quebec, Canada, Vol. 60, G79–G115, May 26–29, 1987. (8) Falk, John Carl, and et al., "Synthesis and Properties of Ethylene-Butylene-1 Block Copolymers", Macromolecules, Vol. 4, No. 2, pp. 152–154, March–April 1971. (9) Morton, Maurice, and et al., "Elastomeric Polydiene ABA Triblock Copolymers within Crystalline End Blocks", University of Arkon, work supported by Grant No. DMR78-09024 from the National Science Foundation and Shell Development Co. (10) Yee, A. F., and et al., "Modification of PS by S-EB-S Block Copolymers: Effect of Block Length", General Electric Corporate Research & Development, Schenectady, N.Y. 12301. (11) Siegfried, D. L., and et al., "Thermoplastic Interpenetrating Polymer Networks of a Triblock Copolymer elastomer and an Ionomeric Plastic Mechanical Behavior", Polymer Engineering and Science, January 1981, Vol. 21, No. 1, pp 39–46. (12) Clair, D. J., "S-EB-S Copolymers Exhibit Improved Wax Compatibility", Adhesives Age, November, 1988. (13) Shell Chemical Technical Bulletin SC: 1102–89, "Kraton® Thermoplastic Rubbers in oil gels", April 1989. (14) Chung P. Park and George P. Clingerman, "Compatibilization of Polyethylene-Polystyrene Blends with Ethylene-Styrene Random Copolymers", the Dow Chemical Company, May 1996. (15) Steve Hoenig, Bob Turley and Bill Van Volkenburgh, "Material Properties and Applications of Ethylene-Styrene Interpolymers", the Dow Chemical Company, September 1996. (16) Y. Wilson Cheung and Martin J. Guest, "Structure, Thermal Transitions and Mechanical Properties of Ethylene/Styrene Copolymers", the Dow Chemical Company, May 1996. (17) Teresa Plumley Kaijala, Y. Wilson Cheung and Martin J. Guest, "Melt Rheology and Processability of Ethylene/Styrene Interpolymers", the Dow Chemical Company, May 1997. (18) D. C. Prevorsek, et al., "Origins of Damage Tolerance in Ultrastrong Polyethylene Fibers and Composites:, Journal of Polymer Science: Polymer Symposia No. 75,81–104 (1993). (19) Chen, H., et al, "Classification of Ethylene-Styrene Interpolymers Based on Comonomer Content", J. Appl. Polym. Sci., 1998, 70, 109. (20–24) U.S. Pat. Nos. 5,872,201; 5,460,818; 5,244,996; EP 415815A; JP07,278,230 describes substantially random, more appropriately presudo-random copolymers (interpolymers), methods of making and their uses. (25) Alizadeh, et al., "Effect of Topological Constraints on The Crystallization Behavior of Ethylene/alpha-Olefin Copolymers", PMSE, Vol, 81, pp. 248–249, Aug. 22–26, 1999. (26) Guest, et al., "Structure/Property Relationships of Semi-Crystalline Ethylene-Styrene Interpolymers (ESI)", PMSE, Vol, 81, pp. 371–372, Aug. 22–26, 1999. (27) A. Weill and R. Pixa, in Journal of Polymer Science Symposium, 58,381–394 (1977), titled: "Styrene-diene Triblock Copolymers: Orientation Conditions and Mechanical Properties of the Oriented Materials" describe techniques of orientation of neat SIS and SBS block copolymers and their properties. (28) Elastomeric Thermoplastic, Vol. 5, pages 416430; Block Copolymers, Vol. 2, pages 324; Block and Graft Copolymers; Styrene-Diene Block Copolymers, Vol. 15, pages 508–530; and Microphase Structure, can be found in *ENCYCLOPEDIA OF POLYMER SCIENCE AND ENGINEERING*, 1987. (29) Legge, N. R, et al., Chemistry and Technology of Block Polymers, Ch. 29, pages 394–429, ACS, Organic Coatings and Plastics Chemistry,© 1975. (30) legge, N. R., Thermoplastic Elastomers, Rubber Chemistry and Technology, Vol. 60, pages G79–117. (31) Lindsay, G. A., et al., Morphology of Low Density Polyethylene/EPDM Blends Having Tensile Strength Synergism, source: unknown. (32) Cowie, J. M. G., et al., Effect of Casting on the Stress-Hardening and Stress-Softening Characteristics of Kraton-G 1650 Copolymer Films, J. Macromol. Sci.-Phys., B16(4), 611–632 (1979). (33) Futamura, S., et al., Effects of Center Block Structure on the Physical and Rheological Properties of ABA Block Copolymers. Part II. Rheological Properties, Polymer Engineering and Science, August, 1977, Vol. 17, No. 8, pages 563–569. (34) Kuraray Co., LTD. MSDS, Kuraray Septon 4055, Hydrogenated Styrene Isoprene/Butadiene Block Copolymer, Apr. 25, 1991. (35) Hoening, et al. U.S. Pat. No. 6,156,842, May 23, 2000, "Structures and fabricated articles having shape memory made from. Alpha.-olefin/vinyl or vinylidene aromatic and/or hindered aliphatic vinyl or vinylidene interpolymers. (36) Shell Technical bulletin SC: 1102–89 Kraton® Thermoplastic Rubbers in oil gels", April 1989. (37) Witco products literature #1610M 700–360: "White oils Petrolatum, Microcrystalline Waxes, Petroleum Distillates", 1996 Witco Corporation. (38) Witco presentation: "White Mineral Oils in Thermoplastic Elastomers", $ANTEC_{2002}$, May 5–8,2002. (39) Lyondell literature LPC-8126 1/93, "Product Descriptions of White Mineral Oils", pp 30–33. (40) Collins, Jr., Henry Hill, 'COMPLETE FIELD GUIDE TO AMERICAN WILDLIFE", 1959, LCCN: 58-8880. (41) Romanack, Mark, Bassin' with the Pros, 2001, LCCN: 2001086512. (42) Salamone, Joseph C., Concise Polymeric Materials Encyclopedia, CRC Press, 1999. (43) Lide, David R., Handbook of Chemistry and Physics, CRC Press, 78th Edition, 1997–1998. (44) Sigma year 2002–2003 Biochemical and Reagents for life Science Research, sigma-aldrich.com. (45) Kraton Polymers and Compounds, Typical Properties Guide, K0137 Brc-00U, 2001. (46) Kraton Thermoplastic Rubber, Typical properties 1988, SC: 68–78, 5/88 5M. (47) Humko chemical Product Guide, Witco 1988. (48) Opportunities with Humko chemical Kemamide fatty amides, Witco1987. The above applications, patents and publications are specifically incorporated herein by reference.

Legge's paper teaches the development of (conventional substantially amorphous elastomer mid segment) SEBS triblock copolymers. In the polymerization of butadiene by alkyllithium initiators, 1,4-addition or 1,2-addition polymers, mixtures, can be obtained. In forming styrene butadiene triblock copolymers involving the addition of solvating agents such as ethers just before the final styrene charge is added, any excess of ethers can alter the polybutadiene structure from a 1,4-cis or trans structure to a 1,2- or 3,4-addition polymer. Using difunctional coupling agent would give linear block copolymers and multifuntional agents would give star-shaped or radial block copolymers. Hydrogenation of the 1,4-polybutadiene structure yields polyethylene, while that of the 1,2-polybutadiene yields polybutylene. The resulting polyethylene will be essentially identical with linear, high-density polyethylene with a melting point, Tm, of about 136° C. Hydrogenation of 1,2-polybutadiene would yield atactic poly(1-butene) (polybutylene). The Tg of polybutylene is around −18° C. Random mixtures of ethylene and butylene units in the chain would suppress crystallinity arising from polyethylene sequences. The objective for a good elastomer should be to obtain a saturated olefin elastomeric segment with the lowest possible Tg and the best elastomeric properties. Such an elastomer favored using styrene as the hard-block monomer and selecting the best monomer for hydrogenation of the elastomer mid segment. Using a mixture of 1,4- and 1,2-polybutadiene as the base polymer for the mid segment would result in an ethylene/butylene mid segment in the final product. The elements of selection of the midsegment composition is elastomer crystallinity and the elastomer Tg of an ethylenelbutylene copolymer. Very low levels of crystallinity can be achieved around 40–50% butylene concentration. The minimum in dynamic hysteresis around 35% butylene concentration in the elastomeric copolymer. A value of 40% butylene concentration in the ethylene/butylene midsegment was chosen for the S-EB-S block copolymers.

Clair's paper teaches that the LB midblock of conventional S-LB-S polymers is a random copolymer of ethylene and 1-butene exhibiting nearly no crystallinity in the midblock. In the preparation of ethylene-butylene (EB) copolymers, the relative proportions of ethylene and butylene in the EB copolymer chain can be controlled over a broad range from almost all ethylene to almost all butylene. When the EB copolymer is nearly all ethylene, the methylene sequences will crystallize exhibiting properties similar to low density polyethylene. In differential scanning calorimeter (DSC) curves, the melting endotherm is seen on heating and a sharp crystallization exotherm is seen on cooling. As the amount of butylene in the EB copolymer is increased, the methylene sequences are interrupted by the ethyl side chains which shorten the methylene sequences length so as to reduce the amount of crystallinity in the EB copolymer. In conventional S-EB-S polymers, the amount of 1-butene is controlled at a high enough level to make the EB copolymer midblock almost totally amorphous so as to make the copolymer rubbery and soluble in hydrocarbon solvents. Clair suggests that an S-EB-S polymer retaining at least some crystallinity in the EB copolymer midblock may be desirable. Therefore, a new family of S-EB-S polymers are developed (U.S. Pat. No. 3,772,234) in which the midblock contains a higher percentage of ethylene. The molecular weights of the new crystalline midblock segment S-EB-S polymers can vary from low molecular weight, intermediate molecular, to high molecular weight; these are designated Shell GR-3, GR-1, and GR-2 respectively. Unexpectly, the highest molecular weight polymer, GR-2 exhibits an anomalously low softening point. A broad melting endotherm is seen in the DSC curves of these polymers. The maximum in this broad endotherm occurs at about 40° C.

Himes, et al., (U.S. Pat. No. 4,880,878) describes SEBS blends with improved resistance to oil absorption. Papers (14)–(17) describes poly(ethylene-styrene) substantially random copolymers (Dow Interpolymers™): Dow S, M and E Series produced by metallocene catalysts, using single site, constrained geometry addition polymerization catalysts resulting in poly(ethylene-styrene) substantially random copolymers with weight average molecular weight (Mw) typically in the range of $1\times10^5$ to $4\times10^5$, and molecular weight distributions (Mw/Mn) in the range of 2 to 5. Paper (18) Prevorsed, et al., using Raman spectroscopy, WAXS, SAXD, and EM analysis interprets damage tolerance of ultrastrong PE fibers attributed to the nano scale composite structure that consists of needle-like-nearly perfect crystals that are covalently bonded to a rubbery matrix with a structure remarkably similar to the structure of NACRE of abalone shells which explains the damage tolerance and impact resistance of PE fibers. PE because of its unique small repeating unit, chain flexibility, ability to undergo solid state transformation of the crystalline phase without breaking primary bonds, and its low glass transition temperature which are responsible for large strain rate effects plays a key role in the damage tolerance and fatigue resistance of structures made of PE fibers. Chen (19) classifies 3 distinct categories of E (approximately 20–50 wt % styrene), M (approximately 50–70 wt % styrene), & S (greater than approximately 70 wt % styrene) substantially random or more appropriately pseudorandom ethylene-styrene copolymers or random copolymers of ethylene and ethylene-styrene dyads. The designated Ethylene-styrene copolymers are: E copolymers (ES 16, ES24, ES27, ES28, ES28, ES30, and ES44 with styrene wt % of 15.7, 23.7, 27.3, 28.1, 39.6 & 43.9 respectively), M copolymers (ES53, ES58, ES62, ES63, and ES69 with styrene wt % of 52.5, 58.1, 62.7, 62.8, and 69.2 respectively and crystallinity, %, DSC, based on copolymer of 37.5, 26.6, 17.4, 22.9, 19.6 and 5.0 respectively), S copolymers (ES72, ES73, and ES74 with styrene wt % of 72.7, 72.8, and 74.3 respectively). The maximum comonomer content for crystallization of about 20% is similar in other ethylene copolymers, such as in ethylene-hexene and ethylene-vinyl acetate copolymers. If the comonomer can enter the crystal lattice, such as in ethylene-propylene, compositions in excess of 20 mol % comonomer can exhibit crystallinity. The molecular weight distribution of these copolymers is narrow, and the comonomer distribution is homogeneous. These copolymers exhibit high crystalline, lamellar morphologies to fringed micellar morphologies of low crystallinity. Crystallinity is determined by DSC measurements using a Rheometric DSC. Specimens weighing between 5 and 10 mg are heated from −80 to 180° C. at a rate of 10° C./min (first heating), held at 190° C. for 3 min, cooled to −80° C. at 10° C./min, held at −80° C. for 3 min, and reheated from −80° C. to 180° C. at 10° C./min (second heating). The crystallinity (wt %) is calculated from the second heating using a heat of fusion of 290 J/g for the polyethylene crystal. Contributing effects of the crystallinity include decrease volume fraction of the amorphous phase, restricted mobility of the amorphous chain segments by the crystalline domains, and higher styrene content of the amorphous phase due to segregation of styrene into the amorphous phase. Table I of this paper shows values of Total Styrene (wt %), aPS (wt %), Styrene (wt %), Styrene (mol %), $10^{-3}$ Mw, Mw/Mn, and Talc (wt %) for Ethylene-styrene copolymers ES16–ES74 while FIGS. 1–12 of this paper shows: (1) melting thermograms of ESI 1st and 2nd heating for ES 16, ES27, ES44, ES53, ES63, & ES74; (2) crystallinity from DSC as a function of comonomer content; (3) Logarithmic plot of the DSC heat of melting vs. Mole % ethylene for ESIs; (4) measured density as a function of styrene content for semicrystalline and amorphous ESIs; (5) % crystallinity from density vs % crystallinity from DSC melting enthalpy; (6) Dynamic mechanical relaxation behavior; (7) Glass transition temperature as a function of wt % ethylene-styrene dyads for semicrystalline and amorphous ESIs; (8) Arrhenius plots of the loss tangent peak temperature for representative semicrystalline and amorphous ESIs; (9) Draw ratio vs engineering strain; (10) Engineering stress-strain curves at 3 strain rates for ES27, ES63 and F5S74; (11) Engineering stress-strain curves of ESIs; (12) Classification scheme of ESIs based on composition. (20) U.S. Pat. No. 5,872,201 describes interpolymers: terpolymers of ethylene/styrene/propylene, ethylene/styrene/4-methyl-1-pentene, ethylene/styrene/hexend-1, ethylene/styrene/octene-1, and ethylene/styrene/norbornene with number average molecular weight (Mn) of from 1,000 to 500,000. (21–24) U.S. Pat. Nos. 5,460,818; 5,244,996; EP 415815A; JP07,278,230 describes substantially random, more appropriately presudo-ramdom copolymers (interpolymers), methods of making and their uses. (25) Alizadeh, et al., find the styrene interpolymers impedes the crystallization of shorter ethylene crystallizable sequences and that two distinct morphological features (lamellae and fringe micellar or clain clusters) are observed in ethylene/styrene (3.4 mol %) as lamella crystals organized in stacks coexisting with interlamellar bridge-like structures. (26) Guest, et al., describes ethylene-styrene copolymers having less than about 45 wt % copolymer styrene being semicrystalline, as evidenced by a melting endotherm in DSC testing (Dupont DSC-901, 10° C./min) data from the second heating curve. Crystallization decreases with increasing styrene content. Based on steric hindrance, styrene unit is excluded from the crystalline region of the copolymers. Transition from semi-crystalline to amorphous solid-state occurs at about 45 to 50 wt % styrene. At low styrene contents (<40%), the copolymers exhibit a relatively well-defined melting process. FIGS. 1–5 of this paper shows (a) DSC data in the T range associated with the melting transition for a range of ESI differing primarily in copolymer styrene content, (b) variation in percent crystallinity (DSC) for ESI as a function of copolymer S content, (c) elastic modulus versus T for selected ESI differing in S content, (d) loss modulus versus T for selected ESI differing in S content, (e) Tensile stress/strain behavior of ESI differing in S content, respectively. (35) Hoening, et al, teaches preparation of interpolymers ESI #1 to #38 having number average molecular weight (Mn) greater than about 1000, from about 5,000 to about 500,000, more specifically from about 10,000 to about 300,000. (36) J. C. Randall, "A Review of High Resolution Liquid $^{13}$Carbon Nuclear Magnetic Resonance Characterizations of Ethylene-Based Polymers" JMS—Review Macromol. Chem. Phys., C29 (2 & 3), 201–317 (1989). (37) Hammond, et al., U.S. Pat. No. 5,618,882 teaches S-EP-S and S-EB/EP-S block copolymer gel compositions. (38) With respect to SEBS gels, U.S. Pat. No. 4,716,183 teaches at col. 1, lines 24–36: "Various compositions within this class of elastomers have different combinations of physical properties . . . . The particular combinations of properties . . . is not predictable . . . . Other factors can produce drastic changes in properties of the final composition." (39) With respect to SEPS and SEB/EPS gels, U.S. Pat. No. 5,618,882 teaches at col. 1, line 27–28:

"The SEPS gels . . . have higher tack than the known SEBS gels . . . ." at col. 2, lines 50–64: "the polyalkylene blocks may be varies from as low as 20% to 100%, proportions of less than 100% being preferably derived from a mixed isoprene/butadiene feedstock which is copolymerized and hydrogenated to produce . . . . Mixed ethylene/propylene: ethylene/butylene polyalkylene blocks . . . . A particularly preferred . . . . Polyalkylene mid-blocks comprising about 60% ethylene/propylene units and about 40% ethylene/butylene units." at col 5, Lines 64–65: "Tensile strength and elongation show a general improvement, especially for EP/EB midblocks" at col 7, Table III and lines 21–22: ". . . set is improved, particularly with EB/EB mid blocks . . . " and at col. 7, lines 25–27: ". . . EP/EB mid block gels show a clear improvement over EB mid block gels." (40) U.S. Pat. No. 5,994,450 at col. 4, lines 31–33 teaches that "Having familiarized himself with various gels available in the art, the inventor considers the gel compositions of John Chen to be the best available in the prior art". The '450 patent further teaches at col 21 and 22, lines 65–67 and lines 1–3 respectively: " . . . triblock polymer of . . . polystyrene . . . hydrogenated poly(isoprene+butadiene) . . . or hydrogenated" as materials useful for making gels. poly(ethylene/butylene+ethylene/propylene).

The polymers useful in forming the gel compositions and articles of the invention comprises high viscosity triblock and branched copolymers. The triblock copolymers have the general configuration A-B-A wherein each A is a glassy polymer end block segment of polystyrene and B is a elastomeric polymer center block segment of poly(ethylene-butylene), poly(ethylene-propylene) or poly(ethylene-ethylene-propylene). The useful high viscosity branched copolymers have the general configuration $(A-B)_n$ wherein A is polystyrene and B is (ethylene-butylene), (ethylene-propylene) or (ethylene-ethylene-propylene) and the subscript n is a number. The B and A portions of the triblock and branched copolymers are incompatible and form a two-phase system consisting of sub-micron domains of glassy polystyrene interconnected by flexible B chains. These domains serve to crosslink and reinforce the structure. This physical elastomeric network structure is reversible, and heating the polymer above the softening point of polystyrene temporarily disrupt the structure, which can be restored by lowering the temperature.

The most preferred gels can be prepared by melt blending an admixture comprising: (I) 100 parts by weight of one or more of a high viscosity triblock or branched copolymers or a mixture of two or more of poly(styrene-ethylene-ethylene-propylene-styrene), poly(styrene-ethylene-butylene-styrene), poly(styrene-ethylene-propylene-styrene), (styrene-ethylene-propylene)$_n$, (styrene-ethylene-butylene)$_n$, and optionally in combination with (II) a selected amount of one or more polymer or copolymer selected from the group consisting of poly(styrene-butadiene-styrene), poly(styrene-butadiene), poly(styrene-isoprene-styrene), poly(styrene-isoprene), poly(styrene-ethylene-propylene), poly(styrene-ethylene-ethylene-propylene-styrene) poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, branched or star-shaped, or multiarm copolymer; and (III) from about 300 to about 1,600 parts by weight of an plasticizing oil.

As used herein, the liner triblock copolymers poly(styrene-ethylene-ethylene-propylene-styrene) is denoted by "SEEPS", poly(styrene-ethylene-butylene-styrene) is denoted by "SEBS", poly(styrene-ethylene-propylene-styrene) is denoted by "SEPS"; and the branched copolymers poly(styrene-ethylene-propylene)$_n$ is denoted by "(SEP)$_n$", and poly(styrene-ethylene-butylene)$_n$ is denoted by "(SEB)$_n$". Branched copolymers are often times conventionally referred to as radial or star-shaped polymers.

Gel compositions of the invention are characterized by gel rigidities of from less than about 20 gram Bloom to about 700 gram Bloom and higher. As used herein, the term "gel rigidity" in gram Bloom is determined by the gram weight required to depress a gel a distance of 4 mm with a piston having a cross-sectional area of 1 square centimeter at 23° C.

It should be noted that when the A to B ratio falls substantially below 31:69, various properties such as elongation, tensile strength, tear resistance and the like can decrease while retaining other desired properties, such as gel rigidity, flexibility, elastic memory.

The high viscosity triblock, radial, star-shaped, and multiarm copolymers in (I) which are suitable for use in the present invention has a typical Brookfield Viscosity value of a 20 weight percent solids solution in toluene at 25° C. of at least about 1,800 cps, and preferably about 2,000 cps or higher. Typically, the Brookfield Viscosity values can range from at least about 1,800 to about 16,000 cps and higher. More typically, the Brookfield Viscosity values can range from at least about 1,800 cps to about 40,000 cps and higher. Still more typically, the Brookfield Viscosity values can range from at least about 1,800 cps to about 80,000 cps and higher. Due to structural variations between the triblock, radial, star-shaped, and multiarm copolymers, the high viscosity branched copolymers useful in the invention, typically, may exhibit a lower Brookfield Viscosity value than its counterpart triblock copolymers. However, when the triblock copolymers are considered as branched, then at equal branch lengths, the solution viscosities of the triblock copolymers and branched copolymers are about the same or equivalent. In other words, the typical Brookfield Viscosity values for branched copolymers of a 20 weight percent solids solution in toluene at 25° C. can be less than their counterpart triblock copolymers.

In all cases, the molecular chain lengths (molecular weights) of the triblock and branch copolymers must be sufficient to meet the high solution Brookfield Viscosities requirements described herein that is necessary for making the extremely soft and strong gel compositions.

The high viscosity triblock and branched copolymers: SEEPS, SEBS, SEPS, (SEB)$_n$, and (SEP)$_n$ can be measured under varying conditions of weight percent solution concentrations in toluene. The most preferred and useful triblock and branched copolymers selected have Brookfield Viscosity values ranging from about 1,800 cps to about 80,000 cps and higher when measured at 20 weight percent solution in toluene at 25° C., about 4,000 cps to about 40,000 cps and higher when measured at 25 weight percent solids solution in toluene. Typical examples of Brookfield Viscosity values for branched copolymers (SEB)$_n$ and (SEP)$_n$ at 25 weight percent solids solution in toluene at 25° C. can range from about 3,500 cps to about 30,000 cps and higher; more typically, about 9,000 cps and higher. Other preferred and acceptable triblock and branched copolymers can exhibit viscosities (as measured with a Brookfield model RVT viscometer at 25° C.) at 10 weight percent solution in toluene of about 400 cps and higher and at 15 weight percent solution in toluene of about 5,600 cps and higher. Other acceptable triblock and branched copolymers can exhibit about 8,000 to about 20,000 cps at 20 weight percent solids solution in toluene at 25° C. Examples of most preferred high viscosity triblock and branched copolymers can have Brookfield viscosities at 5 weight percent solution in toluene at 30° C. of from about 40 to about 50 cps and higher. While less preferred polymers can have a solution viscosity at 10 weight percent solution in toluene at 30° C. of about 59 cps and higher.

The high viscosity triblock, radial, star-shaped, and multiarm copolymer of the invention can have a broad range of styrene end block to ethylene and butylene center block ratio of about 20:80 or less to about 40:60 or higher. Examples of high viscosity triblock copolymers that can be utilized to achieve one or more of the novel properties of the present invention are styrene-ethylene-butylene-styrene block copolymers (SEBS) available from Shell Chemical Company and Pecten Chemical Company (divisions of Shell Oil Company) under trade designations Kraton G 1651, Kraton G 1654X, Kraton G 4600, Kraton G 4609 and the like. Shell Technical Bulletin SC:1393–92 gives solution viscosity as measured with a Brookfield model RVT viscometer at 25° C. for Kraton G 1654X at 10% weight in toluene of approximately 400 cps and at 15% weight in toluene of approximately 5,600 cps. Shell publication SC:68–79 gives solution viscosity at 25° C. for Kraton G 1651 at 20 weight percent in toluene of approximately 2,000 cps. When measured at 5 weight percent solution in toluene at 30° C., the solution viscosity of Kraton G 1651 is about 40. Examples of high viscosity SEBS triblock copolymers includes Kuraray's SELBS 8006 which exhibits a solution viscosity at 5 weight percent at 30° C. of about 51 cps. Kuraray's 4055 SEEPS (styrene-ethylene/ethylene-propylene-styrene) block polymer made from hydrogenated styrene isoprene/butadiene block copolymer or more specifically made from hydrogenated styrene block polymer with 2-methyl-1,3-butadiene and 1,3-butadiene which exhibits a viscosity at 5 weight percent solution in toluene at 30° C. of about 90 mPa-S, at 10 weight percent about 5800 mPa-S, typically from less than about 90 mPa-S to above about 111 mPa-S having a specification of about 90 plus or minus 30 mPa-S. Kuraray's 2006 SEPS polymer exhibits a viscosity at 20 weight percent solution in toluene at 30° C. of about 78,000 cps, at 5 weight percent of about 27 mPa-S, at 10 weight percent of about 1220 mPa-S, and at 20 weight percent 78,000 cps. Kuraray SEPS 2005 polymer exhibits a viscosity at 5 weight percent solution in toluene at 30° C. of about 28 mPa-S, at 10 weight percent of about 1200 mPa-S, and at 20 weight percent 76,000 cps. Other grades of SEBS, SEPS, $(SEB)_n$, $(SEP)_n$ polymers can also be utilized in the present invention provided such polymers exhibits the required high viscosity. Such SEBS polymers include (high viscosity) Kraton G 1855X which has a Specific Gravity of 0.92, Brookfield Viscosity of a 25 weight percent solids solution in toluene at 25° C. of about 40,000 cps or about 8,000 to about 20,000 cps at 20 weight percent solids solution in toluene at 25° C. The viscosity of such polymers can range at 5 weight percent solution in toluene at 30° C. of from less than about 20 mPa-S to above about 800 mPa-s, including values and between values 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 250, 300, 350, 400, 450, 500, 550, 600, 650, 700, 750, 800 and above.

The styrene to ethylene and butylene (S:EB) weight ratios for the Shell designated polymers can have a low range of 20:80 or less. Although the typical ratio values for Kraton G 1651, 4600, and 4609 are approximately about 33:67 and for Kraton G 1855X approximately about 27:73, Kraton G 1654X (a lower molecular weight version of Kraton G 1651 with somewhat lower physical properties such as lower solution and melt viscosity) is approximately about 31:69, these ratios can vary broadly from the typical product specification values. In the case of Kuraray's SEBS polymer 8006 the S:EB weight ratio is about 35:65. In the case of Kuraray's 2005 (S:EP), 2006 (S:EP), and 4055 (S:EEP) the (S:EP) and S:EEP weight ratios are 20, 35 and 30 respectively. Much like S:EB ratios of SEBBS and $(SEB)_n$, the S:EP and S:EEP ratios of very high viscosity SEPS, $(SEP)_n$ copolymers are expected to be about the same and can vary broadly.

The S:EB, S:EP, S:EEP weight ratios of high viscosity SEBS, SEPS, $(SEB)_n$, SEEPS and $(SEP)_n$ useful in forming the gel compositions and articles of the invention can range from lower than about 20:80 to above about 40:60 and higher. More specifically, the values can be 19:81, 20:80, 21:79, 22:78, 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52,49:51, 50:50, 51:49 and etc. Other ratio values of less than 19:81 or higher than 51:49 are also possible. Broadly, the styrene block to elastomeric block ratio of the high viscosity triblock, radial, star-shaped, and multiarm copolymers of the invention is about 20:80 to about 40:60 or higher, less broadly about 31:69 to about 40:60, preferably about 32:68 to about 38:62, more preferably about 32:68 to about 36:64, particularly more preferably about 32:68 to about 34:66, especially more preferably about 33:67 to about 36:64, and most preferably about 33:67. In accordance with the present invention, triblock copolymers such as Kraton G 1654X having ratios of 31:69 or higher can be used and do exhibit about the same physical properties in many respects to Kraton G 1651 while Kraton G 1654X with ratios below 31:69 may also be use, but they are less preferred due to their decrease in the desirable properties of the final gel.

Other polymers and copolymers (in major or minor amounts) can be selectively melt blended with one or more of the high viscosity polymers as mentioned above without substantially decreasing the desired properties; these (II) polymers include (SBS) styrene-butadiene-styrene block copolymers, (SIS) styrene-isoprene-styrene block copolymers, (low styrene content SEBS) styrene-ethylene-butylene-styrene block copolymers, (SEP) styrene-ethylene-propylene block copolymers, (SEPS) styrene-ethylene-propylene-styrene block copolymers, $(SB)_n$ styrene-butadiene and $(SEB)_n$, $(SEBS)_n$, $(SEP)_n$, $(SI)_n$, styrene-isoprene multi-arm, branched or star-shaped copolymers and the like. Still, other (II) polymers include homopolymers which can be utilized in minor amounts; these include: polystyrene, polybutylene, polyethylene, polypropylene and other copolymers and the like disclosed above. Such can also ml EPDM, EPR, EVA, coPP, EMA, EEA, $(EP)_n$, polyolefins copolymers such as Dow Chemical Company's Dowlex 3010, 2021D, 2038, 2042A, 2049, 2049A, 2071, 2077, 2244A, 2262A; Dow Affinity ethylene alpha-olefin resin PL-1840, SE-1400, SM-1300; more suitably: Dow Elite 5100, 5110, 5200, 5400, Primacor 141-XT, 1430, 1420, 1320, 3330, 3150, 2912, 3340, 3460; Dow Attane (ultrp low density ethylene-octene-1-copolymers) 4803, 4801, 4602 disclosed in copending Ser. No. 09/130545; such as metallocene catalyzed ethylene-styrene copolymers disclosed in Ser. No. 09/274498; ethylene-butyl acrylate, ethylene-ethyl acrylate, ethylene-methyl acrylate, ethylene-vinyl acetate, ethylene-vinyl acrylate, ethylene-vinyl alcohol, and high vinyl content poly(styrene-ethylene-butylene-styrene) disclosed in Ser. No. 08/954424.

Representative plasticizer oil gels (polymer+oil) of the invention include: (a) Kraton G1651, G 1654X gels; (b) Kraton G 4600 gels; (c) Kraton G 4609 gels; other suitable high viscosity polymer and oil gels include: (d) Tuftec H 1051 gels; (e) Tuftec H 1041 gels; (f) Tuftec H 1052 gels; (g) Kuraray SEEPS 4055 gel; (h) Kuraray SEBS 8006 gel; (i) Kuraray SEPS 2005 gel; (j) Kuraray SEPS 2006 gel, and (k) Gels made from blends (polyblends) of (a)–(h) with other polymers and copolymers include: (1) SEBS-SBS gels; (2) SEBS-SIS gels; (3) SEBS-(SEP) gels; (4) SEBS-$(SEB)_n$ gels; (5) SEBS-$(SEB)_n$ gels; (6) SEBS-$(SEP)_n$ gels; (7) SEBS-$(SI)_n$ gels; (8) SEBS-(SI) multiarm gels; (9) SEBS-$(SEB)_n$ gels; (10) $(SEB)_n$ star-shaped copolymer gels; (11) gels made from blends of (a)–(k) with other homopolymers include: (12) SEBS/polystyrene gels; (13) SEBS/polybutylene gels; (14) SEBS/polyethylene gels; (14) SEBS/polypropylene gels; (16) SEP/SEBS oil gels (17), SEP/SEPS oil gels (18), SEP/SEPS/SEB oil gels (19), SEPS/SEBS/SEP oil gels (20), SEB/SEBS (21), EB-EP/SEBS (22), SEBS/EB (23), SEBS/EP (24), (25) $(SEB)_n$ gels, (26) $(SEP)_n$ gels, (27) SEEPS gels, and the like.

Representative examples of commercial elastomers that can be formed with plasticizing oils in combination with the high viscosity triblock and branched copolymers described above into suitable gels for use in making the gel compositions and articles of the invention: Shell Kratons D1101, D1102, D1107, D1111, D1112, D1113X, D1114X, D1116, D1117, D1118X, D1122X, D1125X, D1133X, D1135X, D1184, D1188X, D1300X, D1320X, D4122, D4141, D4158, D4240, G1650, G1652, G1657, G1701X, G1702X, G1726X, G1750X, G1765X, FG1901X, FG1921X, D2103, D2109, D2122X, D3202, D3204, D3226, D5298, D5999X, D7340, G1654X, G2701, G2703, G2705, G1706, G2721X, G7155, G7430, G7450, G7523X, G7528X, G7680, G7705, G7702X, G7720, G7722X, G7820, G7821X, G7827, G7890X, G7940. Kuraray's SEEPS, SEP/SEPS or SEP/SEB/SEPS Nos. 1001, 1050, 2002, 2003, 3023, 2007, 2043, 2063, 2050, 2103, 2104, 2105, 4033 (SEEPS), 4044

(SEEPS), 4045 (SEEPS), 4077 (SEEPS), 4099 (SEEPS), 8004 (SEBS), 8007, and the like.

The Kuraray SEPTON 4000 (SEEPS) series block polymers: 4033, 4044, 4055, 4045, 4077, 4099, and the like useful in making the gels of the instant invention are made from hydrogenated styrene isoprene/butadiene styrene block copolymer or more specifically made from hydrogenated styrene block polymer with 2-methyl-1,3-butadiene and 1,3-butadiene. Such poly(styrene-isoprene/butadiene-styrene) polymers, depending on the butadiene structure, when hydrogenated will result in "(SEB/EPS)". In cases where the butadiene structures are controlled, it is appropriate to denote (SEB/EPS) as (SE/EPS) where E/EP is ethylene-ethylene-propylene or more simply as (SEEPS) to indicate that the ethylene (E) of the ethylene-butylene (EB) segment of the midblock (EB/EP) of the (SEB/EPS) block polymer is substantially greater than butylene (B) and the amount of (E) can be sufficient so as to exhibit ethylene crystallinity. As indicated below, it is the presence or absence of the butylene methyl group which can be use to distinguish the SEBS polymer from the SEPS and SEEPS types of polymer. The SEEPS polymer of the invention gel, within the experimental uncertainty, lacks sufficient butylene. The invention gels can comprise (I) SEEPS polymers and other (II) polymers, such as: SEPS, SEBS, SIS, SBS, SEB/EPS and the like.

As taught in my co-pending application Ser. Nos.: 10/273,828 and 10/1999364, and specifically incorporated herein, the unusual properties of the invention SEEPS gels can be attributed to altering different phase or interfacial arrangements of the domains of the multiblock copolymers. The presence of polyethylene and crystallinity in block copolymers can be determined by NMR and DSC.

Physical measurements (NMR and DSC) of typical commercial Kraton G 1651, Septon 2006, Septon 4033 and Septon 4055 block were performed. Two types of 13C NMR spectra data were collected. The gated decoupled experiment provided quantitative data for each type of carbon atom. The DEPT experiment identified each type of carbon atom having attached protons. The DEPT data allowed assignment of the resonances in the gated decoupled experiment, which was then integrated for quantitation of the different types of midblock and end groups in each polymer tested The relative quantities of each type of carbon group in the various polymers were found. The uncertainty associated with these measurements is estimated as±3 percentage units. Only the Kraton 1651 spectrum had resonances below about 20 ppm. These resonances, at 10.7–10.9 ppm, were assigned to the butylene methyl group and distinguish the SEBS polymer from the SEPS and SEEPS types of polymer (36). Only the Septon 2006 spectrum lacked the resonance at about 20 ppm that is characteristic of polyethylene units (defined here as three contiguous $CH_2$ groups), and this feature distinguishes the SEPS polymer from the SEBS and SEEPS polymers (36). There were additional differences between the spectra. The Septon 2006 and the Septon 4033 and 4055 spectra all showed resonances at 20 ppm; whereas the spectrum of Kraton 1651 was missing this resonance. The 20 ppm peak is characteristic of the methyl group of a propylene subunit, which is present in SEPS and SEEPS polymers but absent in the SEBS polymer. There were also a methylene peak, at 24.6 ppm, and a methine peak at 32.8 ppm, in all of the Septon spectra but not in the Kraton 1651 spectra. These resonances also arise from the propylene subunit.

The chemical shifts, relative intensities, and relative integrations were the same for the spectra of the Septon 4033 and Septon 4055, indicating that these two polymeric compositions are identical based on NMR spectroscopy.

DSC of ASTM D3417-99 was modified to provide conditions for the samples to have the best possible chance to exhibit any crystallinity. The protocol was as follows: (1) heat to 140° C. @ 10° C./min., (2) cool to 0° C. @ 2° C./min., (3) place in freezer for 1 week, (4) heat to 140° C. @ 1° C./min, and (5) cool to 0° C. @ 2° C.

This protocol was used with the exception that the samples were left in the freezer for approximately 2 months, instead of 1 week, because the DSC equipment broke during the week after the first run and required some time for repair. This delay is not expected to have negatively impacted the results of the experiment.

Two HDPE reference samples gave clearly defined crystallization exotherms and fusion endotherms, allowing calculation of heats of crystallization and fusion. These results showed that the equipment and methodology were fully functional, and this check was performed daily during DSC operation. Of the samples, only Kraton 1651 showed discernable transitions for both crystallization and fusion. The Septon 2006 showed no discernable transitions, which is consistent with its SEPS structure being entirely amorphous. The Septons 4033 and 4055 showed crystallization exotherms.

The heats of crystallization for the Kraton 1651 and Septons 4033 and 4055 were small, below about 3 J/g, indicating that small amounts of crystallinity are present in these polymers. The DSC data show:

Kraton 1651: crystallization exotherm peak at 18.09° C., crystallization exotherm—mass normalized enthalpy (J/g) of 1.43, fusion endotherm peak at 34.13° C., and Fusion Endotherm—mass normalized enthalphy J/g of 15.17.

Septon 2006: crystallization exotherm peak (not detected), crystallization exotherm—mass normalized enthalpy (not detected), fusion endortherm peak NONE, and Fusion Endotherm—mass normalized enthalphy (not detected).

Septon 4033: crystallization exotherm peak at 2.86° C., crystallization exotherm—mass normalized enthalpy (J/g) of 3.00, fusion endortherm peak (not detected), and Fusion Endotherm—mass normalized enthalphy (not detected).

Septon 4055: crystallization exotherm peak at 14.4° C., crystallization exotherm—mass normalized enthalpy (J/g) of 1.32, fusion endortherm peak (not detected), and Fusion Endotherm—mass normalized enthalphy (not detected).

Aldrich 13813 JU polyethylene reference: crystallization exotherm peak at 119.72° C., crystallization exotherm—mass normalized enthalpy (J/g) of 174.60, fusion endortherm peak at 130.70° C., and Fusion Endotherm—mass normalized enthalphy J/g of 189.90.

The invention gels made from higher viscosity SEEPS copolymers (I) are resistant to breaking when sheared than SEPS triblock copolymer gels. This can be demonstrated by forming a very soft gel, for example 100 parts copolymer to 800 parts plasticizing oil. The soft gel is cut into a strip of 2.5 cm×2.5 cm cross-section, the gel strip is gripped lengthwise tightly in the left hand about its cross-section and an exposed part of the gel strip being gripped lengthwise around its cross-section tightly by the right hand as close to the left hand as possible without stretching. With the two hands gripping the gel strip's cross-section, the hands are moved in opposite directions to shear apart the gel strip at its cross-section. The shearing action by the gripping hands is done at the fastest speed possible as can be performed by human hands. The shearing action is performed at a fraction of a second, possible at about 0.5 seconds. Using this demonstration, the SEEPS copolymer (I) invention gels will not easily break completely apart as would gels formed from SEPS triblock copolymers. In some cases, it will take two, three, or more attempts to shear a high viscosity copolymer (I) gel strip this way. Whereas, a lower viscosity triblock copolymer gel strip can be sheared apart on the first try. For gels made from copolymers with viscosities of 5 wt % solution in Toluene of from less than 2 mPa-S to 500 mPa-S and higher, their shear resistance will decrease with decreasing viscosity.

Hence, it is the selected SEEPS which provides the improved tear and fatigue resistance of the invention gel compositions and articles. SEEPS gels of corresponding rigidity exhibit improved greater tear and greater fatigue resistance over SEPS gels and SEBS gels.

As taught in my co-pending application Ser. Nos.: 09/721,213; 09/130,545; 10/273,828; 09/517,230; 09/412,886; 10/199,9364 and specifically incorporated herein, tear strength and resistance to fatigue of the high viscosity SEEPS gels of the invention at corresponding rigidities are found to be greater than that of SEPS gels. Greater tear and fatigue resistance is also found when SEEPS gels are made in combination with other (II) polymers, such as SEPS, SEBS, SBS, SIS, low viscosity SEBS, lower viscosity SEEPS, PS, PE, PP, $(SI)_n$, $(SB)_n$, $(SEB)_n$, Ashai SB/EBS poly(styrene-butadiene-ethylene-butylene-styrene), and the like.

Plasticizers particularly preferred for use in practicing the present invention are will known in the art, they include rubber processing oils such as paraffinic and naphthenic petroleum oils, highly refined aromatic-free paraffinic and naphthenic food and technical grade white petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight.

Examples of representative commercially available plasticizing oils include Amoco® polybutenes, hydrogenated polybutenes, polybutenes with epoxide functionality at one end of the polybutene polymer, liquid poly(ethylene/butylene), liquid hetero-telechelic polymers of poly(ethylene/butylene/styrene) with epoxidized polyisoprene and poly(ethylene/butylene) with epoxidized polyisoprene: Example of such polybutenes include: L-14 (320 Mn), L-50 (420 Mn), L-100 (460 Mn), H-15 (560 Mn), H-25 (610 Mn), H-35 (660 Mn), H-50 (750 Mn), H-100 (920 Mn), H-300 (1290 Mn), L-14E (27–37 cst @ 100° F. Viscosity), H-300E (635–690 cst @ 210° F. Viscosity), Actipol E6 (365 Mn), E16 (973 Mn), E23 (1433 Mn), Kraton L-1203, EKP-206, EKP-207, HPVM-2203 and the like. Example of various commercially oils include: ARCO Prime (55, 70, 90, 200, 350, 400 and the like), Duraprime and Tufflo oils (6006, 6016, 6016M, 6026, 6036, 6056, 6206, etc), other white mineral oils include: Bayol, Bernol, American, Blandol, Drakeol, Ervol, Gloria, Kaydol, Litetek, Lyondell (Duraprime 55, 70, 90, 200, 350, 400, etc), Marcol, Parol, Peneteck, Primol, Protol, Sontex, and the like. Generally, plasticizing oils with average molecular weights less than about 200 and greater than about 700 may also be used (e.g. H-300 (1290 Mn)).

The gel compositions of the invention can also be made into composites. The gels may be made non-adhearing, non-sticking, (non-tacky), by incorporating an advantage amount of stearic acid (octadecanoic acid) or metal stearates (e.g., calcium stearate, magnesium sterate, zinc stearate, etc.).

An advantage of making non-sticking, non-tacky gels is the use of waxes, stearic acid and waxes, metal sterate and waxes, metal sterate and stearic acid. The use of stearic acid alone do not reduce tack. The amount of stearic acid is also important. As an example, ratio of 200 grams stearic acid to 2,000 gram of SEBS (a ratio of 0.1) will result in spotted tack reduction on the surface of the gel. A ratio of 250 to 2,000 will result in spotted crystallized regions on the surface of the gel or spotted tack reduction. A ratio of 300 to 2,000 will result in complete tack reduction with large stearic acid crystallized regions on the surface of the gel. When microcrystalline waxes are incorporated together with stearic acid, the crystallization of stearic acid completely disappears from the surface of the gel. For example excellent result is achieved with 200 grams of stearic acid, 150 grams of microcrystalline wax and 2,000 grams of SEBS. The same excellent results is achieved when SEBS is adjusted to 3,000 grams, 4,000 grams, etc. The same result is achieved with SEPS, $(SEB)_n$, $(SEP)_n$ polymers.

The present invention also provides oriented gels with improved high strength alignment properties as evidenced by optical techniques such as viewing oriented gel in plane-polarized light. Oriented gels exhibit birefringence in the relaxed unextended state. Oriented gels with improved strength are suitable for use as dental floss since they do not break as easily as un-oriented gels of the same rigidity.

The oriented gels can also contain useful amounts of conventionally employed additives such as stabilizers, antioxidants, antiblocking agents, colorants, fragrances, flame retardants, flavors, other polymers in minor amounts and the like to an extend not affecting or substantially decreasing the desired properties of the invention.

As taught in my application Ser. No. 08/288,690 filed Aug. 11, 1994, now U.S. Pat. No. 5,633,286 and specifically incorporated herein, additives useful in the gel of the present invention include: tetrakis[methylene 3,-(3'5'-di-tertbutyl4"-hydroxyphenyl) propionate] methane, octadecyl 3-(3",5"-di-tert-butyl-4"-hydroxyphenyl) propionate, distearyl-pentaerythritol-diproprionate, thiodiethylene bis-(3,5-ter-butyl-4-hydroxy) hydrocinnamate, (1,3,5-trimethyl-2,4,6-tris[3,5-di-tert-butyl-4-hydroxybenzyl]benzene), 4,4"-methylenebis (2,6-di-tert-butylphenol), stearic acid, oleic acid, stearamide, behenamide, oleamide, erucamide, N,N"-ethylenebisstearde, N,N"-ethylenebisoleamide, sterryl erucamide, erucyl erucamide, oleic palmitamide, stearyl stearamide, erucyl stearamide, calcium sterate, other metal sterates, waxes (e.g. polyethylene, polypropylene, microcrystalline, carnauba, paraffin, montan, candelilla, beeswax, ozokerite, ceresine, and the like). The gel can also contain metallic pigments (aluminum and brass flakes), TiO2, mica, fluorescent dyes and pigments, phosphorescent pigments, aluminatrihydrate, antimony oxide, iron oxides (Fe3O4, —Fe2O3, etc.), iron cobalt oxides, chromium dioxide, iron, barium ferrite, strontium ferrite and other magnetic particle materials, molybdenum, silicone fluids, lake pigments, aluminates, ceramic pigments, ironblues, ultramarines, phthalocynines, azo pigments, carbon blacks, silicon dioxide, silica, clay, feldspar, glass microspheres, barium ferrite, wollastonite and the like. The report of the committee on Magnetic Materials, Publication NMAB-426, National Academy Press (1985) is incorporated herein by reference.

Oriented gels aligned by controlled stretching during the gel's transition from a heated, extremely viscous, non melting, non flowing state and the cooled solid gel state produces strong gels which are found to have greater tensile strength than gels of the same rigidity which have not been stretched to a selected degree during its heating and cooling histories.

Gels which are selectively stretched during its (non melt flowing) heated state and rapidly cooled by flowing air, cold liquid bath or in contact with a cool surface exhibit optical birefringence when viewed under plane-polarized light. The degree of stretching during the gels cooling history from the heated state can vary. Stretching of at least about 50% to more than about 1000% are of advantage to produce birefringence and stronger gels. Birefrigence is not observed in relaxed gels which do not undergo stretching during its heating and cooling histories. Slight to very strong birefrigence are observed in relaxed gels which are stretched during their heating and cooling histories. It is evident that stressing the gel during its cooling history as it cools from the heated state produce unexpected stronger oriented gels. We therefore consider oriented gels to be a new and novel composition physically different from the less stronger gels formed without stressing during the gels cooling history and which do not show birefrigence in the relaxed state. Oriented gels may be formed in combination with various substrates such as described below. In past situations where in order to obtain stronger gel strength, gels with higher rigidities and lower plasticizer content must be used, it is now possible to make a oriented gel with the same plasticizer content having a higher useful gel strength.

The gel compositions and oriented gel compositions of the invention can be casted unto various substrates, such as open cell materials, metals, ceramics, glasses, and plastics, etc.; the molten gel composition is deformed as it is being cooled. Useful open-cell plastics include: polyamides, polyimides, polyesters, polyisocyanurates, polyisocyanates, polyurethanes, poly(vinyl alcohol), etc. Open-celled Plastic (sponges) suitable for use with the compositions of the invention are described in "Expanded Plastics and Related Products", Chemical Technology Review No. 221, Noyes Data Corp., 1983, and "Applied Polymer Science", Organic Coatings and Plastic Chemistry, 1975. These publications are incorporated herein by reference.

The gel compositions denoted as "G" of the invention can be physically interlocked with a selected material denoted as "M" to form composites as denoted for simplicity by their combinations $G_nM_n$, $G_nM_nG_n$, $M_nG_nM_n$, $M_nG_nG_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nM_nM_nG_n$, $G_nG_nM_nM_n$, $G_nG_nM_n$, $G_nM_n$, $G_nM_nG_nG_n$, $G_nG_nM_n$, $G_nM_nG_nM_nM_n$, $M_nG_nM_nG_nM_nG_n$, $G_nG_nM_nM_nG_n$, $G_nG_nM_nG_nM_nG_n$, and the like or an of their permutations of one or more $G_n$ with $M_n$ and the like, wherein when n is a subscript of M, n is the same or different selected from the group consisting of foam, plastic, fabric, metal, concrete, wood, glass, ceramics, synthetic resin, synthetic fibers or refractory materials and the like; wherein when n is a subscript of G, n denotes the same or a different gel rigidity of from about 20 to about 800 gram Bloom). The gel compositions and articles of the composites are formed from I, II, and III components described above.

Sandwiches of gel/material (i.e. gel-material-gel or material-gel-material, etc.) are ideal for use as shock absorbers, acoustical isolators, vibration dampers, vibration isolators, and wrappers. For example the vibration isolators can be use under research microscopes, office equipment, tables, and the like to remove background vibrations.

The gelatinous elastomer compositions and oriented gel compositions are prepared by blending together the components including other additatives as desired at about 23° C. to about 100° C. forming a paste like mixture and further heating said mixture uniformly to about 150° C. to about 200° C. until a homogeneous molten blend is obtained. Lower and higher temperatures can also be utilized depending on the viscosity of the oils and amounts of SEBS, SEPS, $(SEB)_n$, $(SEP)_n$ or mixtures thereof used. These components blend easily in the melt and a heated vessel equipped with a stirrer is all that is required. Small batches can be easily blended in a test tube using a glass stirring rod for mixing. While conventional large vessels with pressure and/or vacuum means can be utilized in forming large batches of the instant compositions in amounts of about 40 lbs or less to 10,000 lbs or more. For example, in a large vessel, inert gases can be employed for removing the composition from a closed vessel at the end of mixing and a partial vacuum can be applied to remove any entrapped bubbles or forced out as is producing naturally foamed gas bubble entrapped gel composition. Stirring rates utilized for large batches can range from about less than 10 rpm to about 40 rpm or higher.

The oriented gelatinous elastomer composition of the invention is excellent for forming the strong gelatinous elastomer articles of the invention. The gelatinous elastomer articles can be formed by blending, injection molding, extruding and other conventional methods. For example, Shapes having various crossection can be extruded; and as the hot exudate is emerging from the extrusion die, the extradate can be stretched, pulled, twisted or in various manner stressed as it is rapidly placed in contact with cooling air, cool water bath, or other cooling media.

The gel compositions can also be formed directly into articles or remelted in any suitable hot melt applicator and extruded or spun into threads, bands, or other shapes. The instant compositions is excellent for cast molding and the molded products have various excellent characteristics which cannot be anticipated form the properties of the raw components. Other conventional methods of forming the composition can be utilized.

As taught in my application Ser. No. 08/288,690 filed Aug. 11, 1994, now U.S. Pat. No. 5,633,286 and specifically incorporated herein, the gelatinous elastomer composition of the invention is excellent for forming the gelatinous elastomer composite articles of the invention. The gelatinous elastomer composite articles can be formed by blending, melting, dipping, casting, injection molding, extruding and other conventional methods. For example, a foam of a preselected pore size can be placed in a mold cavity and a preselected amount of a preselected rigidity of gelatinous elastomer composition is then injected into the mold. The mold is allow to cool to room temperature and the article removed. A preselected rigidity of molten gelatinous elastomer composition can be cast directly onto a section of open cell foam to form the composite article. Likewise, an article of foam can be dipped into a preselected rigidity of molten gelatinous elastomer composition and re-dipped into the same or different composition of a different rigidity. The shaped composite article of the invention can be conventionally covered with protective skins of elastomeric film, fabric or both as needed.

The composition can also be remelted in any suitable hot melt applicator for hot dipping, extrusion, sputtering, or spraying on to the foams or sponges so as to form the gelatinous elastomer composite articles of the invention.

As taught in my application Ser. No. 08/288,690 filed Aug. 11, 1994, now U.S. Pat. No. 5,633,286 and specifically incorporated herein, generally the molten gelatinous elastomer composition will adhere sufficiently to certain plastics (e.g. acrylic, ethylene copolymers, nylon, polybutylene, polycarbonate, polystyrene, polyester, polyethylene, polypropylene, styrene copolymers, and the like) provided the temperature of the molten gelatinous elastomer composition is sufficient high to fuse or nearly fuse with the plastic. In order to obtain sufficient adhesion to glass, ceramics, or certain metals, sufficient temperature is also required (e.g. above 250° F.). Commercial resins which can aid in adhesion to materials (plastics, glass, and metals) may be added in minor amounts to the gelatinous elastomer composition, these resins include: Super Sta-tac, Nevtac, Piccotac, Escorez, Wingtack, Hercotac, Betaprene, Zonarez, Nirez, Piocolyte, Sylvatac, Foral, Pentalyn, Arkon P, Regalrez, Cumar LX, Picco 6000, Nevchem, Piccotex, Kristalex, Piccolastic, LX-1035, and the like. The conventional term "major" means about 51 weight percent and higher (e.g. 55%, 60%, 65%, 70%, 75%, 80% and the like) and the term "minor" means 49 weight percent and lower (e.g. 2%, 5%, 10%, 15%, 20%, 25% and the like to less than 50%)(based on 100 parts of (1)).

The basis of this invention resides in the fact that one or more of a high viscosity triblock or branched copolymers or a mixture of two or more of such copolymers having styrene end block to elastomeric block ratio preferably within the contemplated range of from about 20:80 to about 40:60 and higher, more preferably from between about 31:69 to about 40:60 and higher when blended in the melt with an appropriate amount of plasticizing oil makes possible the attainment of gelatinous elastomer compositions having a desirable combination of physical and mechanical properties, notably high elongation at break of at least 1,600%, ultimate tensile strength of about at least $8 \times 10^5$ dyne/cm$^2$, low elongation set at break of substantially not greater than about 2%, tear resistance of at least $5 \times 10^5$ dyne/cm$^2$, substantially about 100% snap back when extended to 1,200% elongation, and a gel rigidity of substantially from about 20 gram to about 700 gram Bloom and higher.

More specifically, the gelatinous composition of the present invention exhibit one or more of the following properties. These are: (1) tensile strength of about $8 \times 10^5$ dyne/cm$^2$ to about 107 dyne/cm$^2$ and greater; (2) elongation of about 1,600% to about 3,000% and higher; (3) elasticity modulus of about $10^4$ dyne/cm$^2$ to about $10^6$ dyne/cm$^2$ and greater; (4) shear modulus of about $10^4$ dyne/cm$^2$ to about $10^6$ dyne/cm$^2$ and greater as measured with a 1, 2, and 3 kilogram load at 23° C.; (5) gel rigidity of about less than about 20 gram Bloom to about 700 gram Bloom and higher as measured by the gram weight required to depress a gel a distance of 4 mm with a piston having a cross-sectional area of 1 square cm at 23° C.; (6) tear propagation resistance of at least about $5 \times 10^5$ dyne/cm$^2$; (7) and substantially 100% snap back recovery when extended at a crosshead separation speed of 25 cm/minute to 1,200% at 23° C. Properties (1), (2), (3), and (6) above are measured at a crosshead separation speed of 25 cm/minute at 23° C.

The gelatinous elastomer articles molded from the instant compositions and articles have various additional important advantages in that they do not crack, creep, tear, crack, or rupture in flexural, tension, compression, or other deforming conditions of normal use; but rather the molded articles made from the instant composition possess the intrinsic properties of elastic memory enabling the articles to recover and retain its original molded shape after many extreme deformation cycles as compared to prior art triblock copolymer oil-extended compositions. In applications where low rigidity, high elongation, good compression set and excellent tensile strength are important, the instant gel compositions would be preferred.

The gelatinous elastomer compositions and articles of the present invention are useful in low frequency vibration applications, such as viscoelastic layers in constrained-layer damping of mechanical structures and goods, as viscoelastic layers used in laminates for isolation of acoustical and mechanical noise, as anti-vibration elastic support for transporting shock sensitive loads, as vibration isolators for an optical table, as viscoelastic layers used in wrappings, enclosures and linings to control sound, as compositions for use in shock and dielectric encapsulation of optical, electrical, and electronic components. The compositions are also useful as molded shape articles for use in medical and sport health care, such use include therapeutic hand exercising grips, dental floss, crutch cushions, cervical pillows, bed wedge pillows, leg rest, neck cushion, mattress, bed pads, elbow padding, dermal pads, wheelchair cushions, helmet liner, cold and hot packs, exercise weight belts, traction pads and belts, cushions for splints, slings, and braces (for the hand, wrist, finger, forearm, knee, leg, clavicle, shoulder, foot, ankle, neck, back, rib, etc.), and also soles for orthopedic shoes. Other uses may include as toys, optical uses (e.g. cladding for cushioning optical fibers from bending stresses) and various optical devices, as lint removers, dental floss, as tips for swabs, as fishing bait, as a high vacuum seal (against atmosphere pressure) which contains a useful amount of a mineral oil-based magnetic fluid particles, etc.

As an example of the versatility of use of the instant gel compositions, a hand exerciser can be made in any shape so long as it is suitable for use as a hand exerciser: a sphere shape, a cube shape, a rectangular shape, etc. Likewise, a wheelchair cushion can be made from the composition in any shape, so long as it meets the needs of the user of the cushion. For example, a cushion can be made by forming the composition into a selected shape matching the contours of the specific body part or body region. The composition can be formed into any desired shaped, size and thickness suitable as a cushion; the shaped composition can be additionally surrounded with film, fabric, foam, or any other desired material or combinations thereof. Moreover, the composition can be casted onto such materials, provided such materials substantially maintain their integrity (shape, appearance, texture, etc.) during the casting process. The same applies for brace cushions for the hand, wrist, finger, forearm, knee, leg, etc.

Another versatile use of the composition is dental flossing. The dental floss can be almost any shape so long as it is suitable for dental flossing. A thick shaped piece of the composition can be stretched into a thin shape and used for flossing. A thinner shaped piece would require less stretching, etc. The instant compositions can be formed in any shape; the original shape can be deformed into another shape (to contact a regular or irregular surface) by pressure and upon removal of the applied pressure, the composition in the deformed shape will recover back to its original shape.

While preferred components and formulation ranges have been disclosed herein, persons of skill in the art can extend these ranges using appropriate material according to the principles discussed herein. All such variations and deviations which rely on the teachings through which the present invention has advanced the art are considered to be within the spirit and scope of the present invention. The invention is further illustrated by means of the following illustrative embodiments, which are given for purpose of illustration only and are not meant to limit the invention to the particular components and amounts disclosed.

EXAMPLE I

A comparison was made between a low viscosity poly (styrene-ethylene-butylene-styrene) triblock copolymer having styrene end block to ethylene and butylene center block ratio below the range between 31:69 to 40:60 and a high viscosity poly(styrene-ethylene-butylene-styrene) triblock copolymer of the invention. Three different triblock copolymers were melt blended separately with a paraffinic white petroleum oil. Table I below shows the physical properties obtain with respect to each of the different viscosity and styrene to ethylene and butylene ratio triblock copolymer oil-blends tested.

The properties measured are as follows: Tear Propagation (ASTM D 19938 modified), Cracking (ASTM D 518 Method B modified), Tensile Strength (ASTM D 412 modified), Ultimate elongation (ASTM D 412 modified), Tensile Set (ASTM D 412 Modified), Compression Set (ASTM D 395 modified), Snap Back, and Hand Kneading (60 seconds). The methods of measurement are taught in U.S. Pat. Nos. 4, 618,213 and 5,153,254; and, as well as, in copending applications Ser. Nos. 705,711; 934,027 and 935,540.

TABLE I

| Formulation | S/EB Ratio[1] | Weight Parts | | |
|---|---|---|---|---|
| | | A | B | C |
| SEBS[2] | 28:72 | 100 | | |
| SEBS[3] | 29:71 | | 100 | |
| SEBS[4] | 33:67 | | | 100 |
| Paraffinic oil[5] | | 400 | 400 | 400 |
| Stabilizer[6] | | 2.5 | 2.5 | 2.5 |
| Breaking strength[7], dyne/cm$^2$ | | 4 × 10$^5$ | 4 × 10$^5$ | 4 × 10$^6$ |
| Tear propagation[8], dyne/cm$^2$ | | 8 × 10$^4$ | 7 × 10$^4$ | 1 × 10$^6$ |
| Compression set[10] at 24 hours | | 81%(R) | 77%(R) | 0.0% |
| Rigidity, gram Bloom | | 1,536 | 1,520 | 360 |

[1] Styrene to ethylene and butylene ratio
[2] Shell Kraton G1650 having a Brookfield viscosity of 1,500 cps as measured for a 20% weight solids solution in toluene at 25° C.
[3] Shell Kraton G 1652 having a Brookfield viscosity of 550 cps as measured for a 20% weight solids solution in toluene at 25° C.
[4] Shell Kraton G 1651 having a Brookfield viscosity of 2,000 cps as measured for a 20% weight solids solution in toluene at 25° C.
[5] ARCO prime 200, [6] Irganox 1010, [7] ASTM D 412 modified,
[8] ASTM D 1938 modified, [9] ASTM D 412 modified, [10] ASTM D 2395 modified, Ruptured completely The results of Table I show drastically unacceptable poor properties of low viscosity triblock copolymers having styrene to ethylene and butylene ratios and low viscosity which are below the contemplated (preferred) range of the instant invention.

Comparisons of oil extended triblock copolymers have been described in Shell Chemical Company Technical Bulletin SC:1102-89 (April 1989) "KRATON®THERMOPLASTIC RUBBERS IN OIL GELS" which is incorporated herein by reference.

EXAMPLE II

One hundred parts by weight of a high viscosity poly (styrene-ethylene-butylene-styrene) triblock copolymer (Shell Kraton G 1651) having a styrene end block to ethylene and butylene center block ratio of about 33:67 with 0.1 parts by weight of a stabilizer (Irrganox 1010) was melt blended with various quantities of a naphthenic oil (ARCO Tufflo 6024). Samples having the dimensions of 5 cm×5 cm×3 cm were cut and measured for gel rigidity on a modified Bloom gelometer as determined by the gram weight required to depress the gel a distance of 4 mm with a piston having a cross-sectional area of 1 cm$^2$. The average gel rigidity values with respect to various oil concentrations are set forth in Table II below.

TABLE II

| Oil per 100 parts of Triblock copolymer | Gd Rigidity, gram Bloom |
|---|---|
| 360 | 500 |
| 463 | 348 |
| 520 | 280 |
| 615 | 240 |
| 635 | 220 |
| 710 | 172 |
| 838 | 135 |
| 1,587 | 54 |

EXAMPLE III

Example II was repeated except about 980 parts oil was used and the gel rigidity found to about 101 gram Bloom. Other properties measured were: tensile strength at break about 4.4×10$^6$ dyne/cm$^2$, elongation at break about 2,4470%, elasticity modulus about 3.5×10$^4$ dyne/cm$^2$, and shear modulus about 3.7×10$^4$ dyne/cm$^2$. The tensile strength, elongation, elasticity modulus were measured with cross-head separation speed of 25 cm/minute at room temperature. The shear modulus was measured with a 1, 2, and 3 kilogram load at room temperature.

EXAMPLE IV

Example II was repeated except about 520 parts of a polybutene (Amoco Indopol H-300) was used and the gel rigidity found to be about substantially unchanged with respect to use of naphthenic oil alone.

EXAMPLE V

Example II was repeated except about 520 parts of a polypropene (Amoco C-60) was used and the gel rigidity found to be about substantially unchanged with respect to use of naphthenic oil alone.

EXAMPLE VI

Example II was repeated except about 520 parts of a polyterpene (Hercules Piccolyte S10) was used and the gel rigidity found to be about substantially unchanged with respect to use of naphthenic oil alone.

EXAMPLE VII

Example II was repeated except about 360 parts of a combined mixture of 72 parts of a paraffinic oil (ARCO prime 200), 72 pars of a naphthenic oil (ARCO Tufflo 6014), 72 parts of a polybutene oligomer (Amoco Indopol H-200). 72 parts of a polypropene oligomer (Amoco Polypropene C-60), and 72 parts of a polyterpene oligomer (Hercules Piccolyte S10) was used and the gel rigidity found to be about substantially unchanged with respect to the use of naphthenic oil alone.

EXAMPLE VIII

Example III was repeated except 933 parts oil with 147 parts by weight of a high viscosity poly(styrene-ethylene-butylene-styrene) triblock copolymer containing 47 parts of a naphthenic process oil (Shell Kraton G 4609) having a styrene to ethylene and butylene ratio of about 33:67 was used and the physical properties were found to be about substantially unchanged with respect to the components used in Example III.

EXAMPLE IX

Example III was repeated except 933 parts oil with 147 parts by weight of a high viscosity poly(styrene-ethylene-butylene-styrene) triblock copolymer containing 47 parts of a paraffinic white petroleum oil (Shell Kraton G4609) having a styrene to ethylene and butylene ratio of about 33:67 was used and the physical properties were found to be about substantially unchanged with respect to the components used in Example I.

EXAMPLE X

Example I was repeated except about 400 parts of oil was used and the properties measured were: tear propagation about $1.4 \times 10^6$ dyne/cm$^2$, no crack growth in 180° bend under 50 gram load for 5,000 hours at room temperature, tensile strength about $4 \times 10^6$ dyne/cm$^2$, elongation at break about 1,700%, tensile set about 0% at 1,200% elongation, compression set about 0% when tested under 5,000 gram load for 24 hours, and 100% snap back recovery after extension to 1,200%.

Examples XI–XIV-t below illustrate other modes of practice contemplated.

EXAMPLE XI

The procedure of Example II is repeated except Shell Kraton G 1651, poly(styrene-ethylene-butylene-styrene) triblock copolymer is used having a styrene end block to ethylene and butylene center block ratio of about 32:68 and the gel rigidity is found to be within the range of about 20 to about 700 gram Bloom.

EXAMPLE XII

The procedure of Example II is repeated except Shell Kraton G 1651, poly(styrene-ethylene-butylene-styrene) triblock copolymer, is used having a styrene end block to ethylene and butylene center block ratio of about 34:66 and the gel rigidity is found to be within the range of about 20 to about 700 gram Bloom.

EXAMPLE XIII

The procedure of Example II is repeated except Shell Kraton G 1651, poly(styrene-ethylene-butylene-styrene) triblock copolymer, is used having a styrene end block to ethylene and butylene center block ratio of about 36:64 and the gel rigidity is found to be within the range of about 20 to about 700 gram Bloom.

EXAMPLE XIV

The procedure of Example II is repeated except Shell Kraton G 1651, poly(styrene-ethylene-butylene-styrene) triblock copolymer, is used having a styrene end block to ethylene and butylene center block ratio of about 38:62 and the gel rigidity is found to be within the range of about 20 to about 700 gram Bloom.

EXAMPLE XIV-a

The procedure of Example II is repeated except Shell Kraton G 1651, poly(styrene-ethylene-butylene-styrene) triblock copolymer, is used having a styrene end block to ethylene and butylene center block ratio of about 31:69 and the gel rigidity is found to be within the range of about 20 to about 800 gram Bloom.

EXAMPLE XIV-b

The procedure of Example II is repeated except Shell Kraton G 1651, poly(styrene-ethylene-butylene-styrene) triblock copolymer, is used having a styrene end block to ethylene and butylene center block ratio of about 37:63 and the gel rigidity is found to be within the range of about 20 to about 800 gram Bloom.

EXAMPLE XIV-c

The procedure of Example II is repeated except Shell Kraton G 1651, poly(styrene-ethylene-butylene-styrene) triblock copolymer, is used having a styrene end block to ethylene and butylene center block ratio of about 19:81 and the gel rigidity is found to be within the range of about 20 to about 800 gram Bloom.

EXAMPLE XIV-d

The procedure of Example II is repeated except Shell Kraton G 1651, poly(styrene-ethylene-butylene-styrene) triblock copolymer, is used having a styrene end block to ethylene and butylene center block ratio of about 20:80 and the gel rigidity is found to be within the range of about 20 to about 800 gram Bloom.

EXAMPLE XIV-e

The procedure of Example II is repeated except Shell Kraton G 1651, poly(styrene-ethylene-butylene-styrene) triblock copolymer is used having a styrene end block to ethylene and butylene center block ratio of about 38:62 and the gel rigidity is found to be within the range of about 20 to about 800 gram Bloom.

EXAMPLE XIV-f

The procedure of Example II is repeated except Shell Kraton G 1651, poly(styrene-ethylene-butylene-styrene) triblock copolymer, is used having a styrene end block to ethylene and butylene center block ratio of about 29:71 and the gel rigidity is found to be within the range of about 20 to about 800 gram Bloom.

EXAMPLE XIV-g

The procedure of Example II is repeated except Shell Kraton G 1651, poly(styrene-ethylene-butylene-styrene) triblock copolymer, is used having a styrene end block to ethylene and butylene center block ratio of about 26:74 and the gel rigidity is found to be within the range of about 20 to about 800 gram Bloom.

EXAMPLE XIV-h

The procedure of Example II is repeated except Shell Kraton G 1651, poly(styrene-ethylene-butylene-styrene) triblock copolymer, is used having a styrene end block to ethylene and butylene center block ratio of about 22:78 and the gel rigidity is found to be within the range of about 20 to about 800 gram Bloom.

EXAMPLE XIV-i

The procedure of Example II is repeated except Shell Kraton G 1651, poly(styrene-ethylene-butylene-styrene) triblock copolymer, is used having a styrene end block to ethylene and butylene center block ratio of about 25:75 and the gel rigidity is found to be within the range of about 20 to about 800 gram Bloom.

EXAMPLE XIV-j

The procedure of Example II is repeated except Shell Kraton G 1651, poly(styrene-ethylene-butylene-styrene) triblock copolymer, is used having a styrene end block to ethylene and butylene center block ratio of about 26:74 and the gel rigidity is found to be within the range of about 20 to about 800 gram Bloom.

EXAMPLE XIV-k

Example II is repeated except a high viscosity poly (styrene-ethylene-propylene-styrene) polymer having a S:EP ratio of 35:65 and a Brookfield Viscosity at 20 weight percent at 30° C. of about 78,000 cps is used and the gel rigidity found to be found to be within the range of about 20 to about 800 gram Bloom.

EXAMPLE XIV-l

Example II is repeated except a high viscosity poly (styrene-ethylene-propylene-styrene) polymer having a S:EP ratio of 20:80 and a Brookfield Viscosity at 20 weight percent at 30° C. of about 76,000 cps is used and the gel rigidity found to be found to be within the range of about 20 to about 800 gram Bloom.

EXAMPLE XIV-m

Compositions of Example II are continuously extruded into 1 meter length rod shape articles through a 0.05, a 0.1, a 0.2, a 0.4, a 0.8, a 1.0, a 1.5, a 1.8, a 2.0, a 4.0, a 8.0 cm (inside diameter) pipe and the extruded articles are allowed to cool to room temperature. Light from a Spectra Physics Model 155A laser with a wavelength of about 632.80 nm is introduced at one end of each article and the light transmitted therethrough.

EXAMPLE XIV-n

Example II is repeated except a high viscosity star-shaped poly(styrene-ethylene-butylene) block copolymer having a S:EB ratio of 30:70 and a Brookfield Viscosity at 25 weight percent at 25° C. of about 9000 cps is used and the gel rigidity found to be found to be within the range of about 20 to about 800 gram Bloom.

EXAMPLE XIV-o

Example II is repeated except a high viscosity star-shaped poly(styrene-ethylene-propylene) random copolymer having a S:EP ratio of 35:65 and a Brookfield Viscosity at 25 weight percent at 25° C. of about 20,000 cps is used and the gel rigidity found to be found to be within the range of about 20 to about 800 gram Bloom.

EXAMPLE XIV-p

Example II is repeated except the molten composition is casted onto a polyether, a polyester, a surlyn ionomer open cell sponge thereby displacing the air space within the sponge and the gel rigidity is found to be greater than about the sum of the combined rigidity of the composition and sponge alone.

EXAMPLE XIV-q

Example II is repeated except a high viscosity star-shaped mixed poly(styrene-ethylene-propylene) copolymer having a S:EP ratio of 35:65 and a Brookfield Viscosity at 25 weight percent at 25° C. of about 12,000 cps is used and the gel rigidity found to be found to be within the range of about 20 to about 800 gram Bloom.

EXAMPLE XIV-r

Example II is repeated except a high viscosity star-shaped mixed poly(styrene-ethylene-butylene) block copolymer having a S:EB ratio of 35:65 and a Brookfield Viscosity at 25 weight percent at 25° C. of about 9,000 cps is used and the gel rigidity found to be found to be within the range of about 20 to about 800 gram Bloom.

EXAMPLE XIV-s

The composition of Example XXI is casted unto a SCOTFOAM® ⅛" thick: 5, 10, 15, 20, 25, 30, 35, 40, 45, 50, 60, 70, 80, 90, 100, and 200 ppi foam sheet.

EXAMPLE XIV-t

The procedure of Example II is repeated except Shell Kraton G 1855X, poly(styrene-ethylene-butylene-styrene) triblock copolymer is used having a styrene end block to ethylene and butylene center block ratio of about 27:73 and the gel rigidity is found to be within the range of about 10 to about 800 gram Bloom.

EXAMPLE XV

Examples I–XIV, XMV–I,n,o,q,r and t are repeated and the gels are extruded and rapidly stretched up to 800% elongation by hand in a cooled water bath. The resulting gels show birefrigence and greater strength than corresponding unstressed (unstretched) gels.

EXAMPLE XVI

A gelatinous elastomer composition of 100 parts of Kraton G1651 and 400 parts by weight of Duraprime 200 white oil is made according to Example II and extruded and drawn into selected lengths of varying diameters from about 0.01 cm to about 0.25 cm for use as dental floss, the gel rigidity being within the range of about 20 to about 800 gram Bloom.

EXAMPLE XVII

Example XVII is repeated using Kurarary SEPS 2006 copolymer, Kurarary SEEPS 4055 copolymer, a high viscosity $(SEB)_n$ copolymer, and a high viscosity $(SEP)_n$ copolymer, the gel rigidities being within the range of about 20 to about 800 gram Bloom.

While certain features of this invention have been described in detail with respect to various embodiments thereof, it will, of course, be apparent that other modifications can be made within the spirit and scope of this invention, and it is not intended to limit the invention to the exact details shown above except insofar as they are defined in the following claims.

I claim:

1. An article comprising: a gel cushion shape article of manufacture formed from
   (I) 100 parts by weight of one or more block copolymer(s) of poly(styrene-ethylene-ethylene-propylene-styrene) in combination with or without
   (II) a minor amount of one or more polymer(s) or copolymer(s) selected from poly(ethylene/styrene/propylene), poly(ethylene/styrene/4-methyl-1-pentene), poly(ethylene/styrene/hexend-1), poly(ethylene/styrene/octene-1), and poly(ethylene/styrene/norbornene);
   (III) from about 300 to about 1,600 parts by weight of a plasticizing oil; said gel cushion shape article characterized by a gel rigidity of about 20 to about 800 gram Bloom; wherein said gel cushion shape is capable of being deformed by an applied pressure into a deformed cushion shape in contact with a regular or irregular surface and upon removal of said applied pressure recover back to said cushion shape.

2. An article comprising: a gel cushion shape article of manufacture formed from
   (I) 100 parts by weight of one or more block copolymer(s) of the general configuration poly(styrene-ethylene-ethylene-propylene-styrene), and
   (II) from about 300 to about 1,600 parts by weight of an plasticizing oil.

3. An article comprising: a gel cushion shape article of manufacture formed from
   (I) 100 parts by weight of one or more of a block copolymer(s) of the general configuration poly(styrene-ethylene-ethylene-propylene-styrene); wherein at least one of said block copolymer is a high viscosity copolymer having a viscosity value at 5 weight percent solution in toluene at 30° C. of about 90 mpa-S and higher in combination with or without
   (II) a selected amount of one or more polymer or copolymer(s) selected from poly(styrene- butadiene-styrene), poly(styrene-butadiene)$_n$, poly(styrene-isoprene-styrene), poly(styrene-isoprene)$_n$, poly(styrene-ethylene-propylene), poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, poly(styrene-ethylene-butylene/styrene-ethylene-butylene-styrene), poly(styrene-ethylene-propylene/styrene-ethylene-propylene-styrene), polystyrene, polybutylene, poly(ethylene-propylene), poly(ethylene-butylene), polypropylene, or polyethylene, wherein said selected copolymer Is a linear, radial, branched, star-shaped, or multiarm copolymer, and n is an integer greater than one, and
   (III) from about 300 to about 1,600 parts by weight of an plasticizing oil; wherein said gel cushion shape is capable of being deformed by an applied pressure into a deformed cushion shape in contact with a regular or irregular surface and upon removal of said applied pressure recover back to said cushion shape.

4. A gel cushion shape article of manufacture of claim 1, wherein said one or more (II) copolymer(s) is selected from low styrene content copolymer(s) of: poly(styrene-ethylene-butylene-styrene), poly(styrene-ethylene-propylene-styrene), poly(styrene-ethylene-butylene/ethylene-propylene-styrene), and poly(styrene-ethylene-ethylene-propylene-styrene).

5. A gel cushion shape article of manufacture of claim 1, 2, or 3, wherein said (II) copolymer(s) is poly(styrene-ethylene-butylene/styrene-ethylene-butylene-styrene), and poly(styrene-ethylene-propylene/styrene-ethylene-propylene-styrene).

6. A gel cushion shape article of manufacture of claim 1, wherein said (II) copolymer(s) is one or more copolymer(s) selected from poly(styrene-ethylene-butylene/styrene-ethylene-butylene-styrene) and poly(styrene-ethylene-propylene/styrene-ethylene-propylene-styrene), poly(styrene-ethylene-propylene-styrene), and poly(styrene-ethylene-butylene-styrene).

7. An article comprising: a gel cushion shaped article of manufacture formed from
   (I) 100 parts by weight of one or more block copolymer(s) of the general configuration poly(styrene-ethylene-ethylene-propylene-styrene);
   (II) from about 300 to about 1,600 parts by weight of a plasticizing oil; and in combination with or without a minor amount of one or more copolymer(s) selected from poly(ethylene alpha-olefin) copolymers, and ultra low density poly(ethylene-octene-1) copolymers; wherein said cushion having the properties of elastic memory capable of recovery and shape retention after many extreme deformation cycles.

8. A article of comprising: a gel cushion shape article of manufacture formed from
   (I) 100 parts by weight of one or more block copolymer(s) of poly(styrene-ethylene-ethylene-propylene-styrene) in combination with or without
   (II) a minor amount of one or more copolymer(s) selected from poly(ethylene-butyl acrylate), poly(ethylene-ethyl acrylate), poly(ethylene-methyl acrylate), poly(ethylene-vinyl acetate), poly(ethylene-vinyl acrylate), and poly(ethylene-vinyl alcohol);
   (III) from about 300 to about 1,600 parts by weight of an plasticizing oil; wherein said cushion shape article having the properties of elastic memory capable of recovery and shape retention after many extreme deformation cycles.

9. A gel cushion shaped article according to claim 3 or 6, wherein said gel cushion shape is in the shape of a pillow.

10. A gel cushion shape article according to claim 3 or 6, wherein said gel cushion shape is in the shape of a cushion for a hand a wrist, a finger, a forearm, a knee, a leg, a clavicle, a shoulder, a foot, an ankle, a neck, a back, or a clutch cushion.

11. A gel cushion shape article according to claim 2 or 4, wherein said gel cushion shape is a pad for a wrist or a cushion for a hand, a wrist, a finger, a forearm, a knee, a leg, a clavicle, a shoulder, a foot, an ankle, a neck, a back.

12. A gel cushion shape article according to claim 3 or 6, wherein said gel cushion shape is a shape of a mattress.

13. A gel cushion shape article according to claim 3 or 6, wherein said gel cushion shape is a shape of a pillow.

14. A gel cushion shape article according to claim 3, wherein said gel cushion shape is a shape of a wrist cushion.

15. A gel cushion shape article according to claim 3 or 6, wherein said gel cushion shape is useful as a wheelchair cushion.

16. An article comprising; a gel cushion shape article of manufacture formed from
   (I) 100 parts by weight of one or more block copolymer(s) of the general configuration poly(styrene-ethylene-ethylene-propylene-styrene) in combination with or without
   (II) a selected amount of one or more polymer or copolymer selected from poly(styrene-butadiene-styrene), poly(styrene-butadiene)$_n$, poly(styrene-isoprene-styrene), poly(styrene-isoprene)$_n$, poly(styrene-ethylene-propylene), poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, polyethylene, poly(ethylene/styrene/propylene), poly(ethylene/styrene/4-methyl-1-pentene), poly(ethylene/styrene/hexend-1), poly(ethylene/styrene/octene-1), poly(ethylene/styrene/norbornene), high vinyl content poly(styrene-ethylene-butylene-styrene), low styrene content poly(styrene-ethylene-butylene-styrene), poly(styrene-ethylene-butylene/styrene-ethylene-butylene-styrene), and poly(styrene-ethylene-propylene/styrene-ethylene-propylene-styrene), or poly(ethylene-styrene) produced by metallocene catalysts; wherein said selected copolymer is a linear, radial, branched, star-shaped, or multiarm copolymer, and n is an integer greater than one, and
   (III) from about 300 to about 1,600 parts by weight of an plasticizing oil; wherein said gel cushion shape is capable of being deformed by an applied pressure into a deformed cushion shape in contact with a regular or irregular surface and upon removal of said applied pressure recover back to said cushion shape.

17. An article comprising: a gel cushion shape article of manufacture formed from
   (I) 100 parts by weight of one or more of a hydrogenated poly(styrene isoprene/butadiene-styrene) block copolymer(s) of the general configuration poly(styrene-ethylene-ethylene-propylene-styrene) in combination with or without
   (II) a selected amount of one or more polymer or copolymer selected from poly(styrene-butadiene-styrene), poly(styrene-butadiene)$_n$, poly(styrene-isoprene-styrene), poly(styrene-isoprene)$_n$, poly(styrene-ethylene-propylene), poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, poly(styrene-ethylene-butylene/styrene-ethylene-butylene-styrene), poly(ethylene-styrene), poly(ethylene-styrene-propylene), polystyrene, polybutylene, polyethylene, and polypropylene; wherein said selected copolymer is a linear, radial, branched, star-shaped, or multiarm copolymer, and n is an integer greater than one, and
   (III) from about 300 to about 1,600 parts by weight of an plasticizing oil; wherein said gel cushion shape is capable of being deformed by an applied pressure into a deformed cushion shape in contact with a regular or irregular surface and upon removal of said applied pressure recover back to said cushion shape.

18. An article comprising: a gel cushion shape article of manufacture formed from
   (I) 100 parts by weight of one or more of a hydrogenated poly(styrene isoprene/butadiene-styrene) block copolymer(s) of the general configuration poly(styrene-ethylene-ethylene-propylene-styrene) and poly(styrene-ethylene-butylene/ethylene-propylene-styrene), and
   (II) from about 300 to about 1,600 parts by weight of an plasticizing oil.

19. An article comprising: a gel cushion shape article of manufacture formed from
   (I) 100 parts by weight of one or more of a hydrogenated poly(styrene isoprene/butadiene-styrene) block copolymer(s) of the general configuration poly(styrene-ethylene-ethylene-propylene-styrene) in combination with
   (II) a selected amount of one or more copolymer(s) selected from poly(ethylene-styrene), poly(ethylene/styrene/propylene), poly(ethylene/styrene/4-methyl-1-pentene), poly(ethylene/styrene/hexend-1), poly(ethylene/styrene/octene-1), or poly(ethylene/styrene/norbornene), produced by metallocene catalysts, and
   (III) from about 300 to about 1,600 parts by weight of an plasticizing oil; said gelatinous composition characterized by a gel rigidity of about 20 to about 800 gram Bloom; wherein said gel cushion shape is capable of being deformed by an applied pressure into a deformed cushion shape in contact with a regular or irregular surface and upon removal of said applied pressure recover back to said cushion shape.

20. A gel cushion shape article according to claims 1, 5, 6, 7, 8, or 19, wherein said gel cushion shape article is in the shape of a cushion for a hand, a wrist, a finger, a forearm, a knee, a leg, a clavicle, a shoulder, a foot, an ankle, a neck, a back, a clutch cushion or a sole cushion for a shoe; wherein said cushion having the properties of elastic memory capable of recovery and shape retention after many extreme deformation cycles.

* * * * *